United States Patent
Monnin et al.

(10) Patent No.: US 11,946,888 B2
(45) Date of Patent: Apr. 2, 2024

(54) FAULT DETECTION IN A THERMAL SENSOR DEVICE

(71) Applicant: Sensirion AG, Stäfa (CH)

(72) Inventors: Eric Monnin, Stäfa (CH); David Kiliani, Stäfa (CH); Andreas Rüegg, Stäfa (CH); Mark Hornung, Stäfa (CH)

(73) Assignee: Sensirion AG, Stäfa (CH)

( * ) Notice: Subject to any disclaimer, the term of this patent is extended or adjusted under 35 U.S.C. 154(b) by 196 days.

(21) Appl. No.: 17/541,128

(22) Filed: Dec. 2, 2021

(65) Prior Publication Data

US 2022/0178855 A1    Jun. 9, 2022

(30) Foreign Application Priority Data

Dec. 3, 2020    (EP) .................................... 20211460

(51) Int. Cl.
    *G01N 25/18*       (2006.01)
    *G01K 15/00*       (2006.01)
    *G01N 25/00*       (2006.01)
    *G01N 25/20*       (2006.01)

(52) U.S. Cl.
    CPC ........... *G01N 25/18* (2013.01); *G01K 15/007* (2013.01); *G01N 25/00* (2013.01); *G01N 25/005* (2013.01); *G01N 25/20* (2013.01)

(58) Field of Classification Search
    CPC ...... G01N 25/18; G01N 25/00; G01N 25/005; G01N 25/20; G01K 15/007
See application file for complete search history.

(56) References Cited

U.S. PATENT DOCUMENTS

| | | | |
|---|---|---|---|
| 4,944,035 A | 7/1990 | Aagardl et al. |
| 6,019,505 A | 2/2000 | Bonne et al. |
| 6,079,253 A | 6/2000 | Bonne et al. |
| 7,188,519 B2 | 3/2007 | Hornung et al. |
| 7,644,613 B2 | 1/2010 | Mayer et al. |

(Continued)

FOREIGN PATENT DOCUMENTS

| | | |
|---|---|---|
| EP | 0439950 A1 * | 12/1990 |
| EP | 1 972 906 A1 | 9/2008 |
| EP | 3 367 087 A2 | 8/2018 |

*Primary Examiner* — Mirellys Jagan
(74) *Attorney, Agent, or Firm* — Foley & Lardner LLP

(57) ABSTRACT

A thermal sensor device is configured to determine a fluid parameter of a fluid based on the heat transfer behavior of the fluid. The sensor device comprises one or more heaters and means for determining a response of the sensor device to heater power being supplied to the heaters. For detecting sensor faults, the sensor device is operated in two different modes of operation. First and second values ($c_{static}$, $c_{dynamic}$) of the same fluid parameter are determined in the two modes. A fault indicator value (F) is derived by comparing the first and second values. The first mode of operation may be a steady-state mode, the first value ($c_{static}$) being based on a steady-state response of the sensor device to heater power being supplied to the heaters, and the second mode of operation may be a dynamic mode, the second value ($c_{static}$) being based on a transient response.

20 Claims, 5 Drawing Sheets

(56) References Cited

U.S. PATENT DOCUMENTS

| | | | |
|---|---|---|---|
| 2016/0032812 A1* | 2/2016 | Lee | F01N 11/007 |
| | | | 73/114.73 |
| 2016/0061691 A1* | 3/2016 | Stojicevic | G01M 15/102 |
| | | | 73/23.31 |
| 2018/0087954 A1 | 3/2018 | Gonzaga et al. | |
| 2019/0293590 A1 | 9/2019 | Merz et al. | |
| 2020/0200580 A1 | 6/2020 | Hornung et al. | |

* cited by examiner

FAULT DETECTION IN A THERMAL SENSOR DEVICE

CROSS REFERENCE TO RELATED APPLICATIONS

This application claims priority to European appl. No. EP20211460.9, filed Dec. 3, 2020; the contents of which are incorporated by reference herein in their entirety.

TECHNICAL FIELD

The present invention relates to a thermal sensor device for determining a fluid parameter of a fluid in thermal contact with the thermal sensor device based on a heat transfer behavior of the fluid, the thermal sensor device comprising processing circuitry configured to carry out a method for detecting faults of the thermal sensor device. The present invention further relates to a corresponding fault detection method.

PRIOR ART

From the prior art it is known to determine one or more fluid parameters of a fluid, such as its flow rate, its thermal conductivity, and/or its specific heat capacity, using a thermal sensor device comprising a heater and one or more temperature sensors. The heater and the temperature sensors can be disposed on a thin membrane (see, e.g., U.S. Pat. No. 7,188,519B2) or on separate bridges spanning an opening or recess of a substrate (see, e.g., EP3367087A2). The sensor device is exposed to the fluid, the heater is provided with heater power, and the response of the temperature sensors to the heater power is measured. Heat transfer between the heater and the temperature sensors is influenced by heat transfer through the fluid. In this way, fluid parameters can be determined. It is also known to determine a fluid parameter by monitoring the resistance of a heater while heater power is supplied to the heater (see, e.g., U.S. Pat. No. 6,079,253). In this case, the heater itself essentially acts as a temperature sensor for the heater temperature, thus obviating the need for a separate temperature sensor.

Two classes of methods for determining fluid parameters using a thermal sensor device are known. In a first class of methods, the heater is heated with constant power or voltage, or it is heated to a constant temperature, and the resulting response of the sensor device is determined once a steady state has been reached. One or more fluid parameters are then determined from the measured steady-state response. For instance, in U.S. Pat. No. 7,188,519B2, the flow rate and the thermal conductivity of a fluid are determined by a "steady-state method", using two temperature sensors disposed on opposite sides of the heater. As another example, in EP3367087A2, the thermal conductivity and the specific heat capacity of a fluid are determined at zero flow from steady-state measurements at a plurality of different measuring temperatures.

In a second class of methods, the heater is operated with a heating power that varies with time, for instance, periodically, and a time lag or phase difference between the heating power and the response of the sensor device is determined. The measured time lag or phase difference depends on the heat transfer properties of the fluid, and at least one fluid parameter is determined on this basis. Examples are provided in U.S. Pat. Nos. 6,079,253A and 6,019,505A.

It is also known to combine steady-state measurements with dynamic measurements to determine two different fluid parameters. For instance, U.S. Pat. No. 4,944,035A discloses a method for determining both the thermal conductivity and the specific heat capacity of a fluid. A pulse of electrical energy is applied to the heater of a level and duration such that both a transient change and a steady-state temperature change occur in the temperature sensor. The thermal conductivity of the fluid is determined based upon a known relation between the sensor output and the thermal conductivity at steady-state sensor temperature. The specific heat capacity of the fluid is determined based on a known relation among the thermal conductivity, the rate of change of the sensor output during a transient temperature change in the sensor, and the specific heat capacity.

Thermal sensor devices of the above types are sometimes employed in safety-relevant applications, e.g. in medical systems or in devices for leakage detection of flammable or explosive fluids like hydrogen gas. In such applications, measures must be taken to ensure that sensor faults, including excessive sensor drifts, are reliably detected.

Safety-relevant systems must often be certified under to a "Safety Integrity Level (SIL)" standard such as IEC 61508. In order to meet such a standard, it may be necessary to carry out self tests of the system not only at startup of the system, but also at regular intervals during operation of the system.

U.S. Pat. No. 7,644,613B2 discloses a thermal flow sensor that is equipped with a self-test unit for monitoring the device and generating a fault signal in the presence of a malfunction. The self-test unit can, e.g., monitor the integrity of a membrane carrying a heater and temperature sensors, or it can monitor various operational parameters of the device. While the self-test unit is able to detect critical malfunctions, some more subtle faults might go unnoticed.

US20200200580A1 discloses a method for detecting contaminations on a thermal sensor device wherein the transient behavior of a thermal parameter is analyzed. Based on this analysis, a contamination signal is determined. While this method is highly useful for detecting contaminations, it may not be able to detect other kinds of malfunctions.

SUMMARY OF THE INVENTION

It is an object of the present invention to provide a thermal sensor device for determining at least one fluid parameter of a fluid based on a heat transfer behavior of the fluid, the thermal sensor device being configured to reliably detect sensor faults that might compromise accuracy of the determined fluid parameter.

The present invention thus provides a thermal sensor device for determining a fluid parameter of a fluid (e.g., liquid or gas) in thermal contact with the thermal sensor device, the determination of the fluid parameter being based on a heat transfer behavior of the fluid.

The thermal sensor device comprises:
  one or more heaters;
  means for determining a response of the sensor device to heater power supplied to the one or more heaters; and
  processing circuitry for supplying the heater power to the one or more heaters and for processing the response of the sensor device to the heater power in order to determine at least one value of the fluid parameter based on said response.

According to the invention, the processing circuitry is configured to carry out a method for detecting faults of the thermal sensor device. The method comprises the steps of:
  a) operating the thermal sensor device in a first mode of operation to determine a first value of the fluid parameter;

b) operating the thermal sensor device in a second mode of operation to determine a second value of the fluid parameter; and c) deriving a fault indicator value based on a comparison of the first and second values of the fluid parameter.

By operating the thermal sensor device in two different modes of operation, two independent determinations of the same fluid parameter are carried out. Sensor faults, including unacceptable drifts or contaminations, will generally influence the two resulting values of the fluid parameter differently. By comparing the two values, sensor faults can be reliably detected, and appropriate measures can be taken.

As outlined above, the response of the sensor device to the heater power can be determined with one or more temperature sensors that are separate from the heaters, and/or by measuring the resistances of the one or more heaters themselves, the heaters thereby acting as their own temperature sensors. Accordingly, the means for determining a response of the sensor device to heater power may comprise one or more temperature sensors that are separate from the heaters and/or circuitry for measuring a resistance of the one or more heaters, the resistance being indicative of heater temperature.

In preferred embodiments, the first mode of operation is a steady-state mode comprising:

supplying heater power to at least one of the one or more heaters;

obtaining a steady-state response of the sensor device (e.g., of the one or more temperature sensors and/or of the resistances of the one or more heaters) to the heater power; and determining the first value of the fluid parameter based on the measured steady-state response.

For instance, in the first mode, the heater power may be supplied at constant power or constant voltage for a time period that is sufficiently long to establish steady-state temperatures at the one or more temperature sensors or steady-state resistances of the one or more heaters. The heater power or voltage being "constant" does not exclude rapid variations on a time scale that is short compared to the response time of the temperature sensors; for instance, constant heater power or constant voltage can be provided by established techniques like pulse width modulation, which involves rapidly switching heater voltage on and off in a binary manner to establish a certain average voltage level. In other embodiments, the heater power is actively regulated such that the heater temperature or resistance is constant. The resulting steady-state temperatures may be measured. In the alternative or in addition, the voltages or power levels required to establish given steady-state temperatures of the one or more heaters and/or of the one or more temperature sensors may be measured, and/or the voltages or power levels required to establish given resistances of the one or more heaters may be measured. The first value of the fluid parameter can then be determined based on one or more of these measurements. In particular, this may be done by any of the methods known from the prior art.

The second mode of operation may be a dynamic mode comprising:

supplying time-variable heater power to at least one of the one or more heaters;

measuring a transient response of the sensor device (e.g., of the one or more temperature sensors and/or of the resistances of the one or more heaters) to the heater power, in particular, a time lag or phase shift between the changing heater power and the transient response; and determining the second value of the fluid parameter based on the measured transient response.

For instance, in the second mode of operation, the heater power may be varied periodically, causing a periodic response of the temperatures measured by the one or more temperature sensors and/or of the resistances of the one or more heaters. One or more time lags or phase shifts between the heater power and the measured temperatures and/or resistances may then be determined. In other embodiments, the heater power varies over time in some non-periodical manner, and the transient response to this variation is measured. For instance, after the heater power has been suddenly switched on or off, a rise time or fall time until the temperature and/or resistance has reached a certain threshold may be measured, or the transient response to a short, intense heater pulse may be determined. From these responses, the second value of the fluid parameter is determined. Again, this may be done by any of the methods known from the prior art.

If the first mode of operation is a steady-state mode and the second mode is a dynamic mode, sensor faults can be detected in a particularly sensitive and reliable manner. In particular, a steady-state mode is generally more sensitive to sensor faults that cause changes in the thermal conductivity of the sensor structure than a dynamic mode. In contrast, a dynamic mode is generally more sensitive to sensor faults that cause changes in the specific heat capacity of the sensor structure than a steady-state mode. Sensor faults can therefore be detected by comparing determinations of the same fluid parameter by the steady-state and dynamic modes. For instance, a contamination on a heater may cause increased heat dissipation from the heater while causing only a small increase of the total thermal capacity of the sensor device. Therefore, the contamination is likely to manifest itself in an appreciable change of the first value determined by the steady-state mode, while it will have a much smaller influence on the second value determined by the dynamic mode. As another example, the processing circuitry may comprise an oscillator for supplying a clock signal at a reference frequency, and the processing circuitry may be configured to measure the transient response in the dynamic mode relative to the reference frequency. A drift of the oscillator will then cause a change of the second value determined by the dynamic mode while not influencing the first value determined by the steady-state mode.

In the latter example, the processing circuitry may be configured to output the clock signal to external circuitry. This enables differentiation between different causes of a given fault indicator value. For instance, if the fault indicator value changes while the frequency of the clock signal remains the same, a fault of the oscillator can be excluded.

The fluid parameter may be any parameter that is associated with a property of a fluid and is amenable to determination with a thermal sensor of the above-described type. In some embodiments, the fluid parameter may be a material parameter that depends on the composition of the fluid, such as its thermal conductivity, specific heat capacity or thermal diffusivity or any other material parameter that correlates with at least one of these heat-transfer properties of the fluid. For instance, the fluid may be a mixture of at least two known constituents, and the material parameter may be a mixing ratio of the mixture or a concentration of one of the constituents in the mixture. In particular, the material parameter may be a concentration of some gas of interest in a mixture with a known carrier gas, e.g., a hydrogen concentration in air, a fuel concentration in air or a concentration of a medical gas in a mixture with a carrier gas, in particular, in a mixture with an oxygen-containing gas. As another example, the fluid may be a combustible gas, and the material parameter may be a combustion-related parameter of the gas, such as a calorific value, a Wobbe index, or a methane number. It is known that combustion-related parameters correlate with heat-transfer properties of a gas, and various methods for determining combustion-related parameters using a thermal sensor of the above-described type are known from the prior art. In other embodiments, the fluid parameter may be a physical parameter associated with the fluid, in particular, a flow rate of the fluid past the thermal sensor device.

The processing circuitry may comprise a memory in which at least one lookup table is stored, the lookup table correlating at least one measured quantity with the fluid parameter. The measured quantity may be, e.g., a temperature value, an average of different temperature values, a temperature difference, a temperature ratio, a resistance value, an average of different resistance values, a resistance difference, a resistance ratio, a time lag, a phase difference etc. The values stored in the lookup table may have been determined beforehand by a calibration procedure using fluids having known values of the fluid parameter.

In particularly simple embodiments, the fault indicator value may be a difference or ratio of the first and second values of the fluid parameter. In other embodiments, the fault indicator value is a value that correlates with said difference or ratio in some other manner. For instance, the fault indicator value may be a value that is computed from the difference or ratio or whose value is set in some other manner according to the difference or ratio.

In some embodiments, the processing circuitry may be configured to obtain at least one auxiliary parameter, such as ambient temperature, pressure and/or (if the fluid is a gas) humidity of the fluid, from at least one auxiliary sensor element. For instance, the thermal sensor device may itself comprise the auxiliary sensor element, or the auxiliary sensor element may be separate from the sensor device. The processing circuitry may be configured to take the obtained auxiliary parameter into account in the determination of the first and second values of the material parameter. In particular, the processing circuitry may be configured to compensate for variations in temperature of the fluid, variations in its pressure and/or variations in its humidity. For instance, the processing circuitry may be configured to determine the first and second values of the fluid parameter for some standard temperature, standard pressure and/or standard humidity, which may be different from the actual temperature, pressure and humidity during the measurements. It is then advantageous if the correlations of the first and second values with the obtained auxiliary parameter are different, i.e., if the uncompensated measured values in the first and second modes of operation exhibit different sensitivities to variations in temperature, pressure and/or humidity of the fluid and therefore different temperature, pressure and/or humidity compensations need to applied during calculation of the compensated first and second values. In this manner the method that is implemented by the processing circuitry becomes not only sensitive to faults that involve the heaters and temperature sensors used for characterizing the heat transfer behavior of the fluid, but also to faults of the auxiliary sensor elements.

Often sensor faults do not occur suddenly, but accumulate gradually until at some point in time they reach a level where the sensor must be replaced. In order to accommodate for such situations and enable predictive maintenance, the processing circuitry may be configured to carry out the steps of: repeating steps a) to c) at a plurality of different times; and based on the fault indicator values at different times, extrapolating a predicted fault indicator value at a later time or determining a predicted time interval until the fault indicator value reaches a threshold.

In order to implement this, the processing device may comprise a memory configured to store a plurality of fault indicator values acquired at different times, and the processing circuitry may be configured to carry out the steps of:
storing a current fault indicator value in the memory;
retrieving fault indicator values that were stored at earlier times from the memory.

In other embodiments, the processing device may keep a variable that is updated "on the fly" each time a new fault indicator value has been determined to carry out said extrapolation or prediction.

The processing circuitry may be configured to output the fault indicator value to external circuitry via an interface of the sensor device. The interface may provide a wired or wireless connection. In the alternative or in addition to outputting the fault indicator value itself, a parameter derived therefrom may be outputted. In particular, the outputted parameter may be a Boolean alarm indicator value. For instance, the alarm indicator value may be set to "True" if the fault indicator has exceeded a preset threshold or if the fault indicator exhibits some atypical behavior such as a sudden rise. The thermal sensor device may comprise a dedicated output contact for outputting the fault parameter or the parameter derived therefrom. This increases reliability of the fault detection mechanism implemented by the present invention.

The two modes of operation of the sensor device may be carried out using the same or different heaters and, where applicable, same or different temperature sensors. In preferred embodiments, the processing circuitry is configured to supply the heater power to the same heater or heaters in both the first mode of operation and the second mode of operation, and/or the processing circuitry is configured to measure the responses of the same temperature sensor or temperature sensors to the heater power in both the first mode of operation and the second mode of operation.

In advantageous embodiments, the one or more heaters, the one or more temperature sensors (where applicable), optionally the one or more auxiliary sensors (where applicable) and at least a portion of the processing circuitry are integrated on a common silicon chip. In particular, at least driver circuitry for the one or more heaters and, where applicable, readout circuitry for the one or more temperature sensors are advantageously implemented on the same chip on which also the heaters and sensors are implemented. While it is possible to implement some or all of the algorithms for deriving the first and second values of the fluid parameter and the fault indicator value in external circuitry, it is preferred that also these algorithms are implemented on the same chip as the heaters and sensors.

The present invention is particularly valuable for thermal sensor devices whose heaters and/or temperature sensors are implemented by patterned polysilicon layers, since polysilicon may have unfavorable ageing characteristics, necessitating close monitoring of the sensor quality.

In another aspect, the present invention provides a method for detecting malfunctions of a thermal sensor device comprising one or more heaters, means for determining a response of the sensor device to heater power supplied to the one or more heaters, and processing circuitry for supplying the heater power and for processing the response of the sensor device to the heater power in order to determine, based on said response, at least one value of a fluid parameter of a fluid in thermal contact with the sensor device. The method comprises:

a) operating the thermal sensor device in a first mode of operation to determine a first value of the fluid parameter;

b) operating the thermal sensor device in a second mode of operation to determine a second value of the fluid parameter; and c) deriving a fault indicator value based on a comparison of the first and second values of the fluid parameter.

The same considerations as for the device according to the present invention also apply to the method of the present invention. In particular, the first mode of operation may be a steady-state mode comprising:

supplying heater power to at least one of the one or more heaters;

measuring a steady-state response of at least one of the one or more temperature sensors to the heater power; and determining the first value of the fluid parameter based on the measured steady-state response, and the second mode of operation may be a dynamic mode comprising:

supplying heater power to at least one of the one or more heaters;

measuring a transient response of at least one of the one or more temperature sensors to the heater power, in particular, a time lag or phase shift between the heater power and the transient response; and determining the second value of the fluid parameter based on the measured transient response.

The method may comprise a step of measuring at least one auxiliary parameter, e.g., ambient temperature, pressure and/or humidity of the fluid, and the measured auxiliary parameter may be taken into account in the determination of the first and second values of the fluid parameter, the first value having a different correlation with the measured auxiliary parameter than the second value.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Thermal Sensor Device with Membrane

Figure 1:
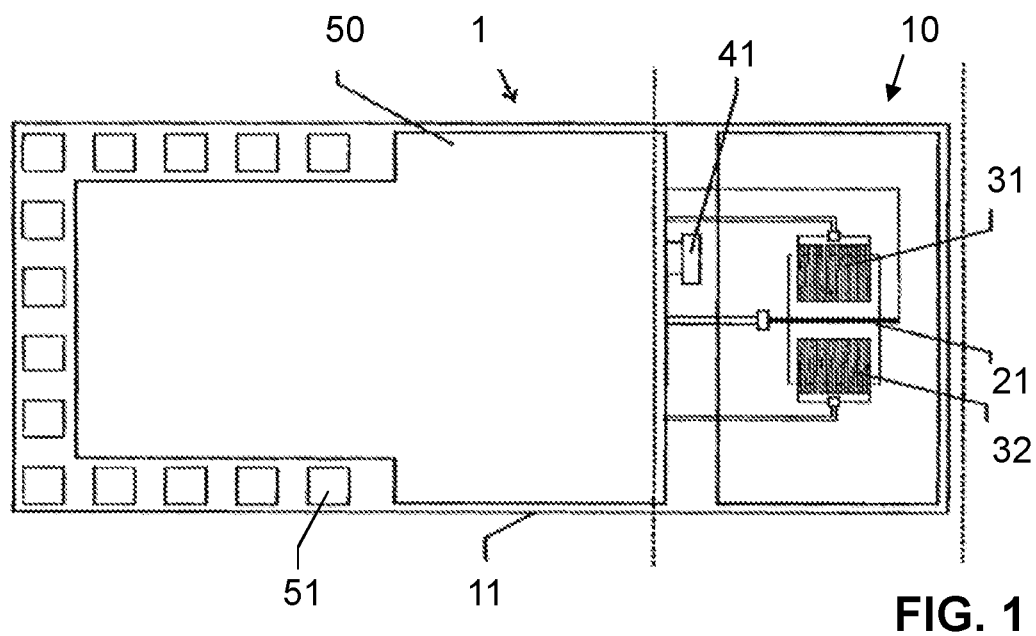
FIG. 1 shows, in a schematic top view, a first embodiment of a thermal sensor device as it is known from the prior art.
Figure 2:
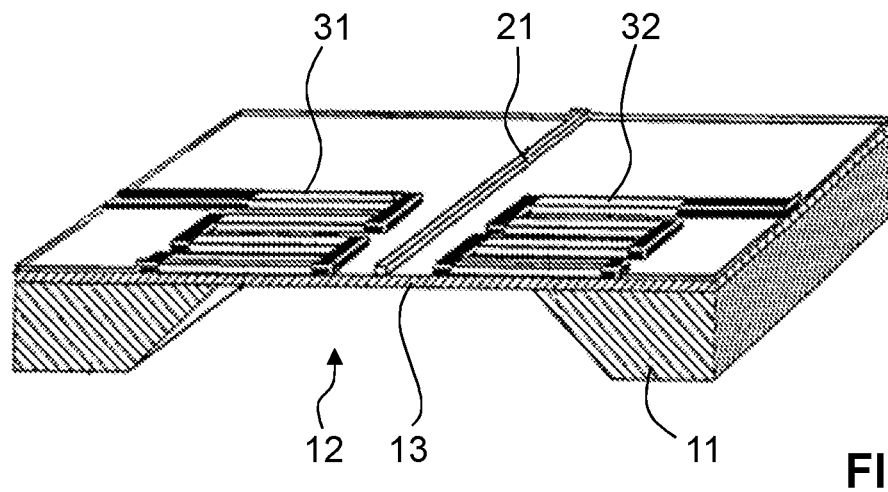
FIG. 2 shows, in a schematic perspective view, part of the sensor element of the thermal sensor device of the first embodiment.

FIGS. 1 and 2 illustrate a thermal sensor device 1 according to a first embodiment. The setup of such a sensor device is disclosed in U.S. Pat. No. 7,188,519B2.

The thermal sensor device 1 comprises a microthermal sensor element 10 and processing circuitry 50 integrated on a common silicon chip 11. Contact pads 51 are provided for interfacing the flow sensor 1 with external circuitry. FIG. 2 shows a portion of the sensor element 10 in a perspective view.

The silicon chip comprises a stack of dielectric layers, metal layers and polysilicon layers. The processing circuitry is formed in this layer stack by a CMOS process. For creating the sensor element 10, a resistive heater 21, a first temperature sensor 31 and a second temperature sensor 32 are formed in or on the layer stack. In the region of the heater 21 and the temperature sensors 31, 32, an opening or recess 12 is etched into the silicon chip 11 from below such that a thin dielectric membrane 13 remains, the membrane spanning the opening or recess 12. At least a portion of the heater 21 and of each temperature sensor 31, 32 is arranged on or in the membrane. In the present example, each of the temperature sensors 31, 32 consists of a thermopile, one set of junctions being disposed on the membrane and the other set of junctions being disposed on the surrounding bulk chip material. Instead, another type of temperature sensor can be used, e.g., resistive temperature sensors.

The sensor element 10 is connected to the processing circuitry 50. The processing circuitry provides heater current to the heater 21 and reads out the temperature sensors 31, 32. In addition, the processing circuitry may be configured to determine the resistance of the heater 21.

Also connected to the processing circuitry 50 is a reference temperature sensor 41 for determining the temperature of the bulk material of the silicon chip 11 that surrounds the membrane. In thermal equilibrium, this temperature will be approximately equal to the ambient temperature of the surrounding fluid. Further auxiliary sensors may be connected to the processing circuitry 50 for determining further auxiliary parameters, such as a pressure sensor for sensing the pressure of the fluid or a relative humidity sensor for sensing relative humidity of the fluid.

Thermal Sensor Device with Bridges

Figure 3:
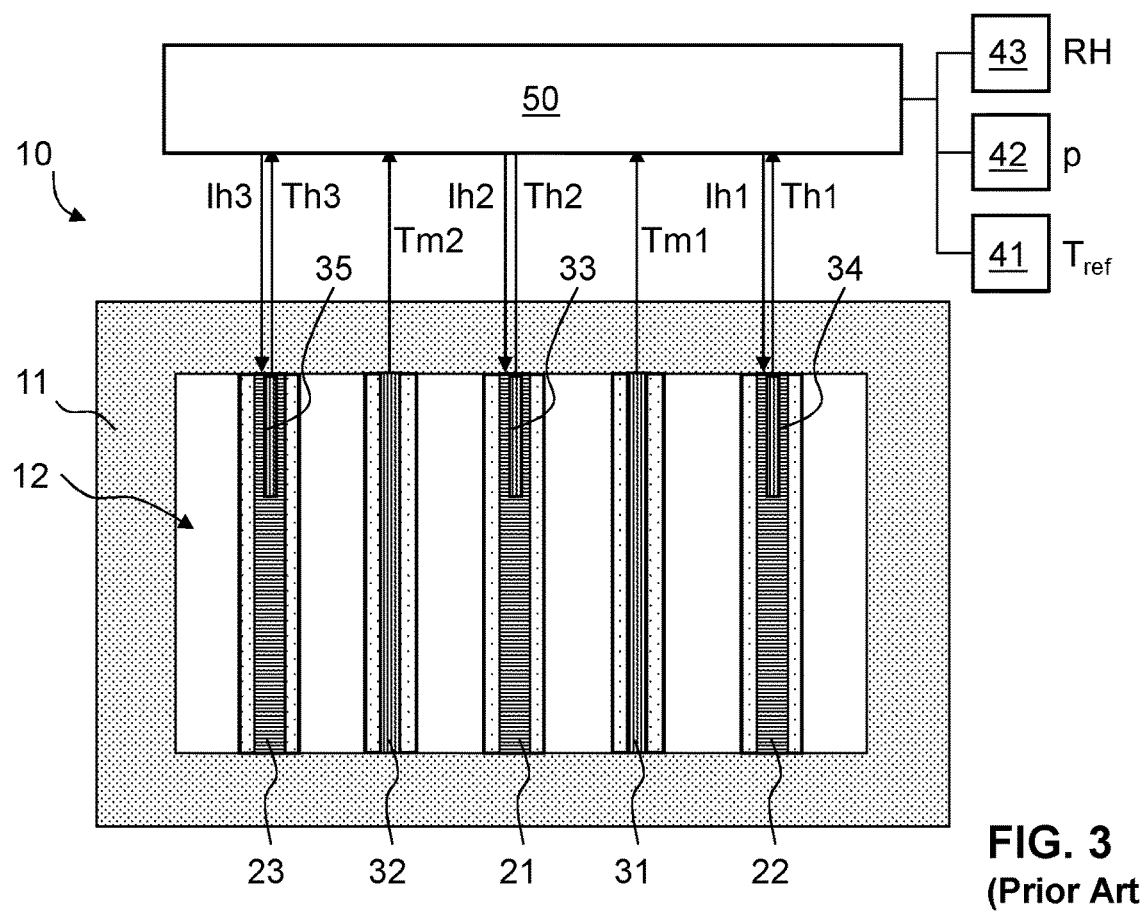
FIG. 3 shows, in a schematic sketch, a second embodiment of a thermal sensor device as it is known from the prior art.

FIG. 3 shows, in a schematic manner, a thermal sensor device according to a second embodiment. The setup of such a sensor device is disclosed in EP3367087A2.

As in the first embodiment, the thermal sensor device comprises a microthermal sensor element 10 connected to processing circuitry 50. Again, for creating the sensor element 10, an opening or recess 12 has been formed in the silicon chip 11. However, instead of an integral membrane, a plurality of bridges span this opening or recess 12, the bridges being separated by voids. Similar to the membrane of the first embodiment, each bridge may be formed by a plurality of dielectric layers, metal layers and/or polysilicon layers patterned from a layer stack on the silicon chip 11.

In the present example, five bridges are present. Three of the bridges are heater bridges, carrying heaters 21, 22, 23, respectively. The processing circuitry 50 supplies the heaters with heater currents Ih1, Ih2 and Ih3, respectively. The heater bridges carry heater temperature sensors 33, 34, 35 for measuring the resulting heater temperatures Th1, Th2 and Th3, respectively. In the alternative or additionally, the processing circuitry may be configured to determine the resistance of each heater element 21, 22, 23 for the purpose of determining heater temperatures. The other two bridges are sensing bridges, carrying temperature sensors 31, 32 for measuring temperatures Tm1 and Tm2, respectively. Each sensing bridge is arranged between two of the heater bridges. While in the present example three heater bridges and two sensing bridges are present, different numbers of heater and sensing bridges may be provided. For instance, only one single heater bridge an only one single sensor bridge may be provided. Furthermore, while in the present example all bridges have the same distance from each other, these distances may also be unequal.

As in the first embodiment, a reference temperature sensor 41 for determining a reference temperature Tref that is indicative of the ambient temperature of the surrounding fluid is connected to the processing circuitry 50. Also connected to the processing circuitry are a pressure sensor 42 for determining a pressure parameter p of the fluid and a relative humidity sensor 43 for determining a humidity parameter RH of the fluid. The temperature sensor, the pressure sensor and the humidity sensor may be provided on the same chip or on a different chip than the sensor element 10.

Processing Circuitry

Figure 4:
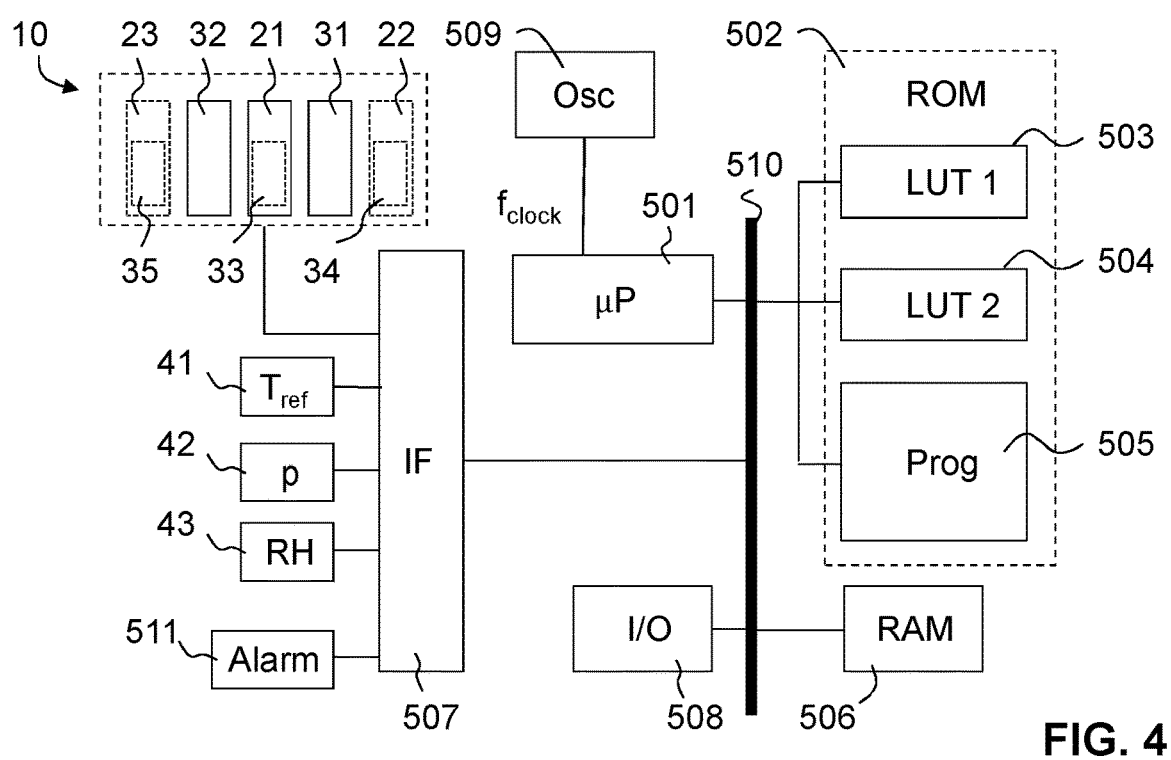
FIG. 4 shows a schematic block diagram of an embodiment of processing circuitry that may be used to implement the present invention.

FIG. 4 illustrates, in a highly schematic manner, a block diagram of a possible embodiment of the processing circuitry 50 of the first or second embodiment. The processing circuitry comprises a processor (μP) 501, a non-volatile (e.g., Flash ROM) memory 502, and a volatile (RAM) memory 506. The processor μP communicates with the memory devices 502, 506 via a bus 510. The non-volatile memory 502 stores, inter alia, plural lookup tables (LUT), only two such lookup tables 503, 504 being illustrated. The non-volatile memory 202 further stores a machine-executable program (Prog) 505 for execution in the processor μP. Via a device interface (IF) 507, the processing circuitry 50 drives the heater elements 21-23 and communicates with the various integrated or external sensors 31-35 and 41-43. A wired or wireless input/output interface I/O 208 enables communication to the outside world. An oscillator (Osc) 509 provides a clock signal with frequency $f_{clock}$ to the processor 501. The oscillator may have an output contact that allows the clock signal to be directly read out by external circuitry. A dedicated alarm contact 511 enables the output of a binary value representing a Boolean alarm indicator value, as will be explained in more detail below.

The processing circuitry 50 may be completely integrated on the same silicon chip as the sensing element 10, or at least parts of the processing circuitry 50 may be implemented separately from the sensing element 10.

Operation

In operation, the sensor element 10 is exposed to a fluid of interest. The processing circuitry provides heater power to the heaters 21-23 and measures the resulting temperatures of the temperature sensors 31-35 and/or the resulting resistances of the heaters 21-23. The processing circuitry also measures the reference temperature $T_{ref}$, the pressure parameter p and the humidity parameter RH, using the auxiliary sensors 41-43.

Figure 5A:
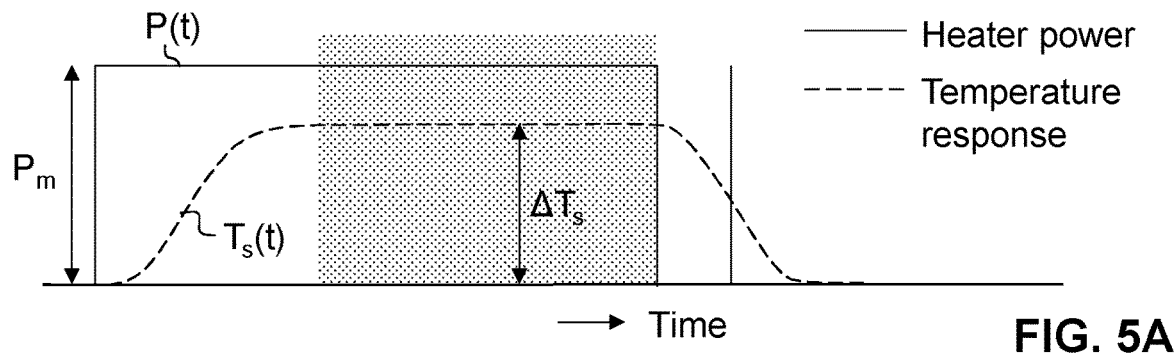
FIG. 5A shows a diagram illustrating a first, steady-state mode of operation of a thermal sensor device.
Figure 5B:
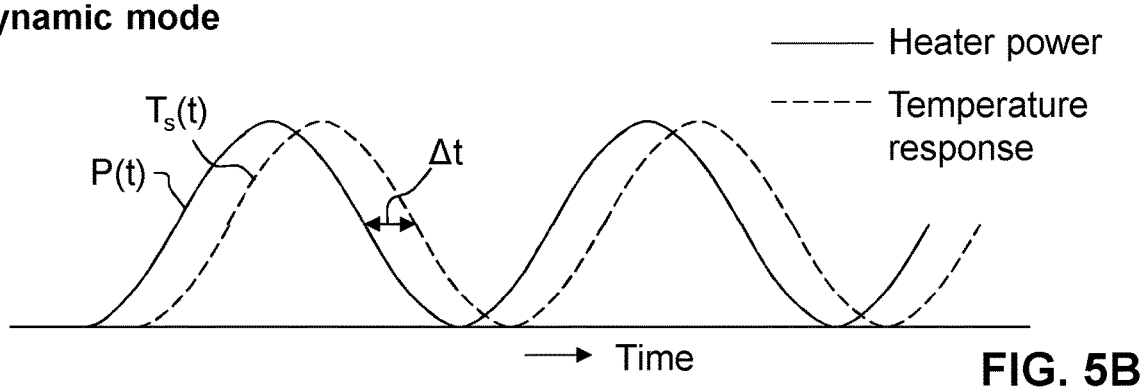
FIG. 5B shows a diagram illustrating a second, dynamic mode of operation of a thermal sensor device.

The processing circuitry carries out two different modes of operation, as illustrated schematically in FIGS. 5A and 5B.

First Mode of Operation

The first mode of operation is a steady-state mode, as illustrated in FIG. 5A. Heater power is switched on and provided for a sufficiently long time that the temperatures measured by the temperature sensors 31-35 and/or the resistances of the heaters 21-23 reach a steady state, and these temperatures and/or resistances are measured.

For instance, in the first embodiment, a heater power P(t) may be applied to the heater 21. Initially, the heater power is zero. At some point in time, the heater power is switched on and is kept constant at a value $P_m$. The resulting temperatures at the temperature sensors 31, 32 are measured. From these temperatures, a linear combination may be formed, for instance, their sum. In FIG. 5A, this sum is designated as $T_s(T)$. This sum will change over time until it reaches a steady-state value. In FIG. 5A, the difference between the steady-state values of this sum after and before switching on the heater power is designated as $\Delta T_s$.

Likewise, in the second embodiment, constant power may be applied to one or more of the heaters 21-23, and the steady-state responses of the temperature sensors 31-35 and/or of the heater resistances may be measured. Combinations of the measured values may again be formed. These combinations or, more generally speaking, intermediate values may of course be more complex than a simple sum. In both embodiments, instead of applying a predetermined power, a predetermined voltage or current may be applied, or the heater power may be regulated to obtain a predetermined heater temperature.

From the measured values and/or from the intermediate values, the processing circuitry 50 determines a first value of a fluid parameter associated with the fluid of interest. To this end, the processing circuitry may use one or more of the lookup tables.

For instance, in the first embodiment, lookup table 503 may correlate $\Delta T_s$ to thermal conductivity of the fluid of interest. This correlation may have been determined beforehand by calibration measurements. Using the lookup table 503, the processing circuitry 50 may determine a first value for the thermal conductivity of the fluid, the first value being based to the measured value of $\Delta T_s$.

Second Mode of Operation

The second mode of operation is a dynamic mode, as illustrated in FIG. 5B. Heater power is varied as a function of time. The transient response of the temperature sensors 31-35 and/or of the resistances of the heaters 21-23 is measured.

For instance, in the first embodiment, a heater power P(t) may again be applied to heater 21. In the second mode of operation, the heater power P(t) now varies periodically, in the present example, sinusoidally. The transient response of the sum signal $T_s(t)$ from temperature sensors 31, 32 is now measured. In FIG. 5B, this transient response has been normalized such that its amplitude in the graph is the same as the amplitude of the heater power P(t). A time lag Δt or, equivalently, a phase difference between the heater power P(t) and the sum signal $T_s(t)$ is determined.

In the second embodiment, one or more time lags or phase differences between heater power and the response of the temperature sensors or heater resistances may likewise be determined.

From the measured time lags or phase differences and/or from intermediate values that have been calculated therefrom, the processing circuitry 50 determines a second value of the fluid parameter. To this end, the processing circuitry may use one or more additional lookup tables.

For instance, in the first embodiment, lookup table 504 may correlate the time lag Δt to thermal conductivity. Again, this correlation may have been determined beforehand by calibration measurements. Using the lookup table 504, the processing circuitry 50 may determine a second value for the thermal conductivity of the fluid, the second value being based to the measured value of Δt.

Determination of Concentration or Mixing Ratio

If the fluid is a mixture of known constituents, knowledge of the thermal conductivity of the fluid allows an inference about the mixing ratio of the fluid or, equivalently, about the concentration of one of the constituents of the fluid.

For instance, if the fluid is a mixture of hydrogen and air, knowledge of the thermal conductivity of the fluid allows an inference about the hydrogen concentration because the thermal conductivity of hydrogen is much larger than the thermal conductivity of air.

Correction for Auxiliary Parameters

The processing circuitry may correct the first and second values of the fluid parameter for variations of auxiliary parameters like ambient temperature, pressure and/or humidity of the fluid.

For instance, the processing circuitry may correct first and second values of the thermal conductivity of the fluid, as determined by the first and second modes of operation of the sensor device, for deviations of the auxiliary parameters from standard conditions, as determined by the auxiliary sensors 41-43. In this manner, the processing circuitry may determine first and second thermal conductivity values at standard conditions.

As another example, if the processing circuitry determines a concentration of a constituent of a mixture, the exact correlation between thermal conductivity and concentration may only be known at standard conditions, and therefore correction of the first and second values for deviations of the auxiliary parameters from standard conditions may be a prerequisite for obtaining a sufficiently precise value of the concentration.

Figure 6:
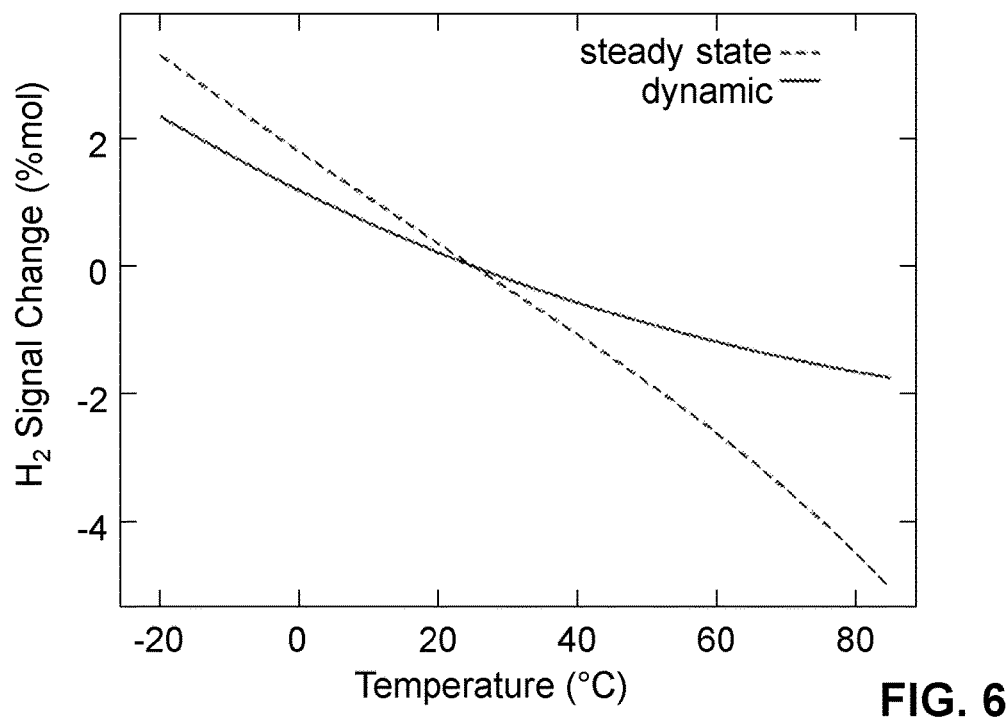
FIG. 6 shows a diagram illustrating a dependence of the change of a hydrogen concentration signal on temperature for measurements in steady-state and dynamic mode.
Figure 7:
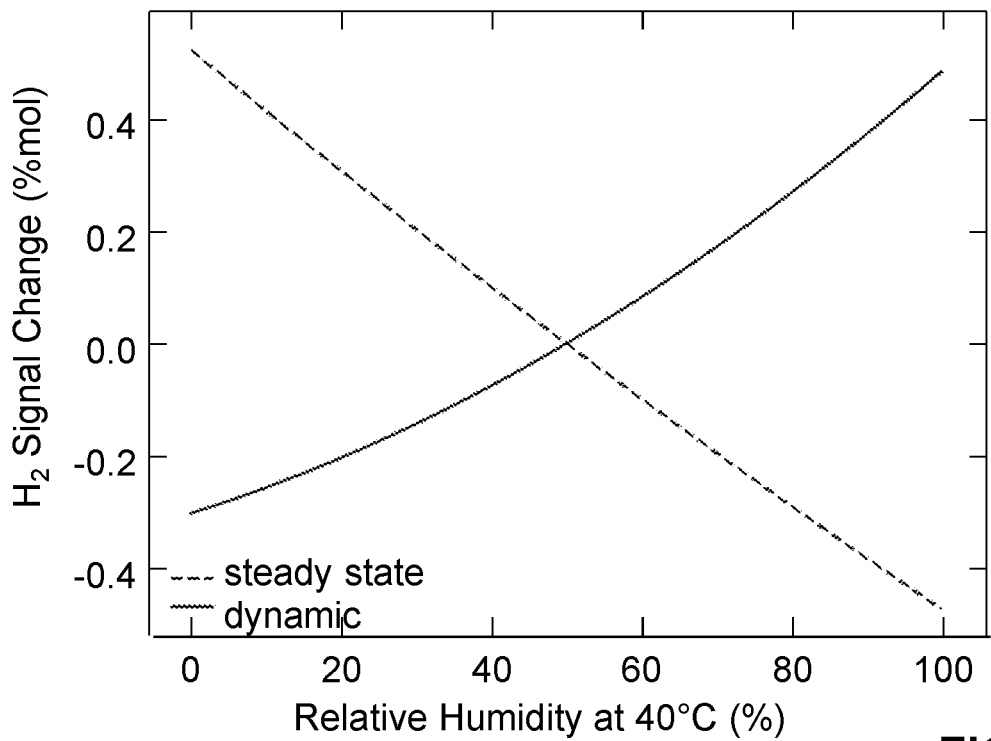
FIG. 7 shows a diagram illustrating a dependence of the change of a hydrogen concentration signal on relative humidity for measurements in steady-state and dynamic mode.
Figure 8:
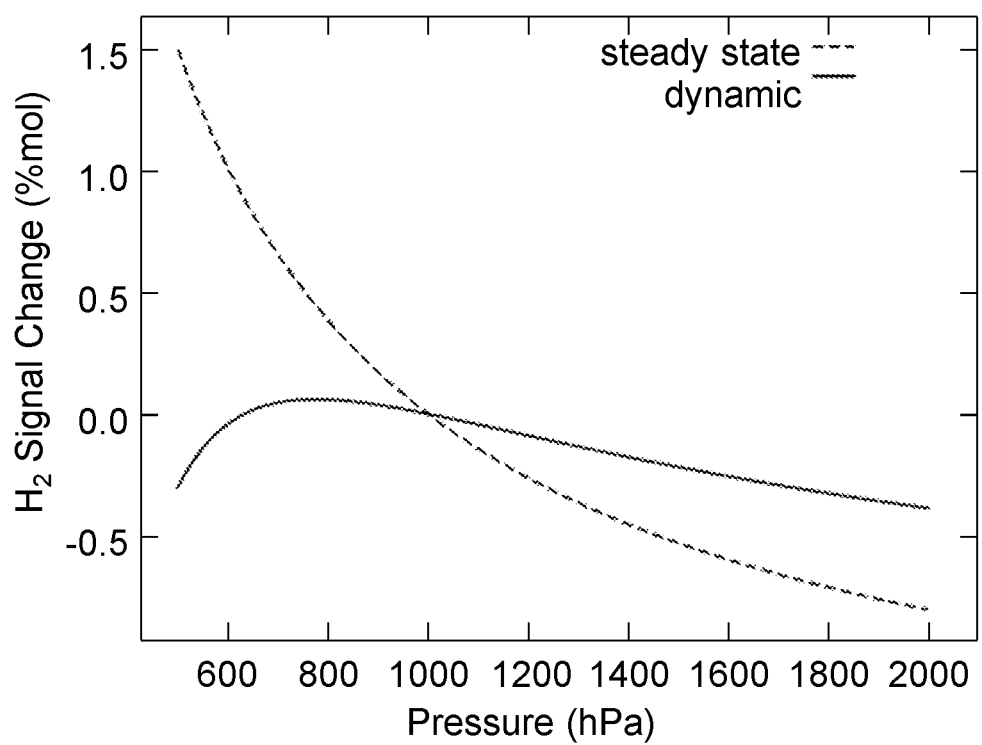
FIG. 8 shows a diagram illustrating a dependence of the change of a hydrogen concentration signal on pressure for measurements in steady-state and dynamic mode.

This is explained in more detail with reference to FIGS. 6 to 8. FIG. 6 illustrates the dependencies of the apparent hydrogen concentration in a mixture of hydrogen and air on temperature, as determined by the first and second modes of operation, if no temperature correction is applied. The broken line shows the temperature dependence of the uncorrected apparent hydrogen concentration value as determined by the first mode of operation (steady state), while the solid line shows the temperature dependence of the uncorrected apparent hydrogen concentration value as determined by the second mode of operation. As can be seen from FIG. 6, the uncorrected apparent concentration values determined by both modes of operation strongly depend on temperature. For instance, if the device has been calibrated at 25° C. and the true hydrogen concentration is 0% mol, a measurement at 0° C., using the first mode of operation, would yield an apparent hydrogen concentration of approximately 2%. This may be unacceptable, and correction ("temperature compensation") may therefore be needed.

As also can be seen from FIG. 6, the dependencies of the apparent concentration values on temperature are different for the first and second modes of operation. Therefore, different corrections ("compensations") should be applied to the values determined by the first and second modes of operation.

Similarly, the determined hydrogen concentration values also depend on relative humidity and pressure. Again, the dependencies are different for the first and second modes of operation, and different corrections ("compensations") should therefore be applied to the values determined by the first and second modes.

Determination of Average

The processing circuitry 50 may calculate an average of the first and second values of the fluid parameter and output the average to external circuitry through the I/O interface 508.

Determination of Fault Indicator Value

As outlined above, the processing circuitry determines first and second values of the same fluid parameter associated with the fluid of interest, the first value being determined by a steady-state mode of operation while the second value is determined by a dynamic mode of operation. Theoretically, these values should be identical. Substantial deviations between these values therefore indicate sensor faults such as drifts or contaminations.

This opens up the possibility for the processing circuitry to calculate a fault indicator value. In the simplest case, the fault indicator value is simply the difference between the first and second values or the absolute value of this difference. However, the fault indicator value may also be a more complex function of these values.

For instance, if the first and second values are concentration values, the fault indicator value may be the absolute value of the difference between these concentration values.

It is to be noted that the fault indicator value will not only reflect faults of the sensor element 10, but also malfunctions of the auxiliary sensors 41-43 because of the different corrections that are applied to the first and second values of the fluid parameter. While this might on first sight seem disadvantageous because it might not be possible to distinguish between faults of the sensor element 10 and faults of the auxiliary sensors 41-43, this is actually an advantage in safety-relevant applications: Any fault in the sensor device, regardless of its cause, will be reflected by the fault indicator value. Monitoring the fault indicator value therefore enables highly reliable failure detection regardless of the cause of the failure. Once a failure has been detected, appropriate measures may be taken, such as replacing the sensor device.

Determination of Alarm Indicator Value

The processing circuitry may monitor the fault indicator value and set an alarm indicator to an alarm value if the fault indicator value meets certain criteria. For instance, the alarm indicator may be a Boolean variable, whose value is set to "True" once the fault indicator value has exceeded a predetermined threshold or once the fault indicator value has started to increase more rapidly between subsequent determinations than expected. The processing circuitry may output the alarm indicator value via the dedicated alarm contact 511.

Predictive Maintenance

The processing circuitry 50 may monitor the fault indicator value at different times and extrapolate an expected future value of the flow indicator or predict a predicted time to failure using past values. To this end, the ROM 502 may comprise a memory portion reserved for storing past fault indicator values, and the processing circuitry may read such past values and use them together with the most recent value to carry out the extrapolation or prediction. The processing circuitry may output the extrapolated future value or the predicted time to failure to external circuitry via the I/O interface 508.

Flow Chart

Figure 9:
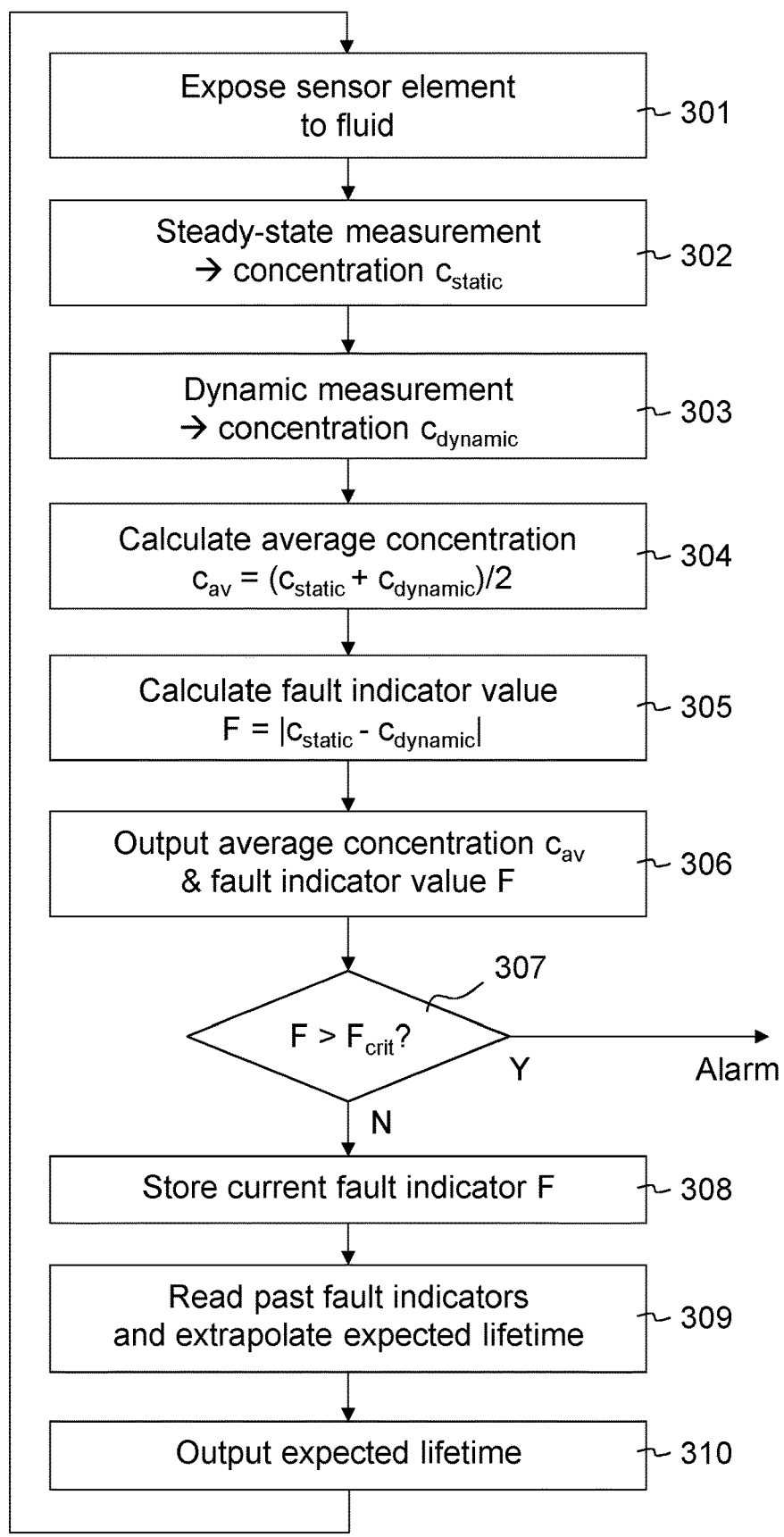
FIG. 9 shows a flow chart illustrating a sequence of steps according to an embodiment of the present invention.

The above-described operation of the sensor device is summarized as a flow chart in FIG. 9. As in the above examples, it is assumed that the fluid parameter determined by the sensor device is a concentration of a constituent of a gas mixture.

In step 301, the sensor element 10 is exposed to the gas mixture. In step 302, the sensor device is operated to carry out a steady-state measurement to determine a first value $c_{static}$ of the concentration. In step 303, the sensor device is operated to carry out a dynamic measurement to determine a second value $c_{dynamic}$ of the concentration. Each of steps 302 and 303 includes an appropriate correction for deviations from standard conditions, using the auxiliary sensors 41-43, as described above. In step 304, an average concentration $c_{av}=(c_{static}+c_{dynamic})/2$ is calculated. In step 305, a fault indicator $F=|c_{static}-c_{dynamic}|$ is calculated. In step 306, the average concentration and the fault indicator are outputted through the I/O interface to external circuitry for further processing. In decision step 307, it is checked whether the fault indicator F has exceeded a threshold $F_{crit}$. In the affirmative, an alarm is triggered by setting the alarm indicator value accordingly. In step 308, the current fault indicator value is stored in memory. In step 309, past flow indicator values are retrieved from memory, and the expected remaining lifetime (predicted time to failure) is computed. In step 310, the expected lifetime is outputted via I/O interface 508.

Modifications

While preferred embodiments of the invention have been described, it is to be understood that the invention is not limited to these embodiments, and that various modifications are possible without leaving the scope of the present invention.

In particular, while the invention has been explained by the way of example of the determination of a concentration or mixing ratio, the thermal sensor device may also be configured to determine other fluid parameters, including other material parameters that are associated with the composition of the fluid as well as physical parameters associated with the fluid, in particular, its flow rate.

The invention is not limited to the above-described examples of thermal sensor devices. The invention is applicable to any thermal sensor device that comprises at least one heater and means for determining a response to heater power being applied to the heater.

While in the above embodiments it was assumed that the entire processing circuitry is integrated on the same silicon chip as the heaters and temperature sensors, some of the functionalities of the processing circuitry may also be implemented externally, e.g., in the form of software that is executed on external hardware. In particular, it is conceivable that the on-chip control circuitry only implements drivers for the heaters and readout circuitry for the temperature sensors and/or resistance values, while all further computations are carried out by external circuitry.

The invention claimed is:

1. A thermal sensor device for determining a fluid parameter associated with a fluid in thermal contact with the thermal sensor device based on a heat transfer behavior of the fluid, the thermal sensor device comprising:

one or more heaters;
means for determining a response of the sensor device to heater power being supplied to the one or more heaters; and
processing circuitry for supplying the heater power and for processing the response of the sensor device to determine at least one value of the fluid parameter based on said response,
the processing circuitry being configured to carry out a method for detecting faults of the thermal sensor device comprising the steps of:
a) operating the thermal sensor device in a first mode of operation to determine a first value of the fluid parameter;
b) operating the thermal sensor device in a second mode of operation to determine a second value of the fluid parameter; and
c) deriving a fault indicator value based on a comparison of the first and second values of the fluid parameter.

2. The thermal sensor device of claim 1, wherein the means for determining a response of the sensor device to heater power comprise one or more temperature sensors, and/or wherein the means for determining a response of the sensor device to heater power comprise circuitry for measuring a resistance of the one or more heaters.

3. The thermal sensor device of claim 1, wherein the fault indicator value correlates with a difference or ratio of the first and second values of the fluid parameter.

4. The thermal sensor device of claim 1,
wherein the processing circuitry is configured to carry out the steps of:
repeating steps a) to c) at a plurality of different times; and
based on the fault indicator values at the different times, extrapolating a predicted fault indicator value at a later time or determining a predicted time interval until the fault indicator value reaches a threshold.

5. The thermal sensor device of claim 1, wherein the one or more heaters and at least a portion of the processing circuitry are integrated on a common silicon chip.

6. The thermal sensor device of claim 1,
wherein the fluid parameter is a material parameter that correlates with at least one of thermal conductivity, specific heat capacity and thermal diffusivity of the fluid.

7. The thermal sensor device of claim 6, wherein the fluid is a mixture of at least two constituents, and wherein the fluid parameter is a mixing ratio of the mixture or a concentration of one of the constituents in the mixture.

8. The thermal sensor device of claim 1, wherein the processing circuitry is configured to obtain at least one auxiliary parameter from at least one auxiliary sensor element, and
wherein the processing circuitry is configured to take the auxiliary parameter into account in the determination of the first and second values of the fluid parameter, the first value having a different correlation with the auxiliary parameter than the second value.

9. The thermal sensor device of claim 8, wherein the at least one auxiliary parameter is ambient temperature, pressure and/or humidity of the fluid.

10. The thermal sensor device of claim 1, wherein the processing circuitry is configured to output the fault indicator value or a parameter derived therefrom.

11. The thermal sensor device of claim 10, comprising a dedicated contact for outputting the fault indicator value or the parameter derived therefrom.

12. The thermal sensor device of claim 10, wherein the processing circuitry is configured to derive a Boolean alarm indicator value from the fault indicator value and to output the Boolean alarm indicator value.

13. The thermal sensor device of claim 1,
wherein the first mode of operation is a steady-state mode comprising:
supplying heater power to at least one of the one or more heaters;
measuring a steady-state response of the sensor device to the heater power using the means for determining a response of the sensor device to heater power; and
determining the first value of the fluid parameter based on the measured steady-state response,
and wherein the second mode of operation is a dynamic mode comprising:
supplying time-variable heater power to at least one of the one or more heaters;
measuring a transient response of the sensor device to the heater power using the means for determining a response of the sensor device to heater power; and
determining the second value of the fluid parameter based on the measured transient response.

14. The thermal sensor device of claim 13,
wherein the processing circuitry comprises an oscillator for supplying a clock signal at a reference frequency,
wherein the processing circuitry is configured to measure the transient response in the second mode of operation relative to the reference frequency, and
wherein the processing circuitry is configured to output the clock signal.

15. The thermal sensor device of claim 13,
wherein the processing circuitry is configured to supply the heater power to the same heater or heaters in both the first mode of operation and the second mode of operation.

16. The thermal sensor device of claim 13,
wherein the means for determining a response of the sensor device to heater power comprise one or more temperature sensors, and wherein the processing circuitry is configured to measure the responses of the one or more temperature sensors to the heater power in both the first mode of operation and the second mode of operation.

17. A method for detecting faults of a thermal sensor device comprising one or more heaters, means for determining a response of the sensor device to heater power being supplied to the one or more heaters, and processing circuitry for supplying the heater power and for processing the response of the sensor device to the heater power in order to determine, based on said response, at least one value of a fluid parameter of a fluid in thermal contact with the sensor device, the method comprising:
a) operating the thermal sensor device in a first mode of operation to determine a first value of the fluid parameter;
b) operating the thermal sensor device in a second mode of operation to determine a second value of the fluid parameter; and
c) deriving a fault indicator value based on a comparison of the first and second values of the fluid parameter.

18. The method of claim 17,
wherein the first mode of operation is a steady-state mode comprising:
supplying heater power to at least one of the one or more heaters;
measuring a steady-state response of the sensor device to the heater power using the means for determining a response of the sensor device to heater power; and
determining the first value of the fluid parameter based on the measured steady-state response,
and wherein the second mode of operation is a dynamic mode comprising:
supplying heater power to at least one of the one or more heaters;
measuring a transient response of the sensor device to the heater power; and
determining the second value of the fluid parameter based on the measured transient response.

19. The method of claim 17,
comprising a step of measuring at least one auxiliary parameter,
wherein the auxiliary parameter is taken into account in the determination of the first and second values of the fluid parameter, the first value having a different correlation with the auxiliary parameter than the second value.

20. The method of claim 19, wherein the at least one auxiliary parameter is ambient temperature, pressure and/or humidity of the fluid.

* * * * *